United States Patent
Gonzalez-Martin et al.

(10) Patent No.: US 6,805,788 B1
(45) Date of Patent: *Oct. 19, 2004

(54) ELECTROCHEMICAL IMPEDANCE EVALUATION AND INSPECTION SENSOR

(75) Inventors: Anuncia Gonzalez-Martin, San Jose, CA (US); Jinseong Kim, College Station, TX (US); Dalibor Hodko, College Station, TX (US); Carlos Salinas, Bryan, TX (US)

(73) Assignee: Lynntech, Inc., College Station, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 936 days.

(21) Appl. No.: 09/113,925
(22) Filed: Jul. 10, 1998
(51) Int. Cl.[7] .............................................. G01N 21/26
(52) U.S. Cl. ..................... 205/775.5; 204/400; 204/404; 204/434
(58) Field of Search ................................ 204/400, 404, 204/434, 421–429; 205/775.5

(56) References Cited

U.S. PATENT DOCUMENTS

| | | | | |
|---|---|---|---|---|
| 3,619,381 A | * | 11/1971 | Fitterer | 204/423 |
| 3,819,500 A | * | 6/1974 | Van Esdonk et al. | 204/426 |
| 3,887,194 A | * | 6/1975 | Porter et al. | 204/415 |
| 4,046,661 A | * | 9/1977 | Stringer et al. | 204/422 |
| 4,155,828 A | * | 5/1979 | Takao et al. | 204/426 |
| 4,445,990 A | | 5/1984 | Kim | |
| 4,800,165 A | | 1/1989 | Oka | |
| 4,806,849 A | | 2/1989 | Kihira | |
| 4,824,528 A | * | 4/1989 | Polak et al. | 204/424 |
| 4,881,037 A | | 11/1989 | Bellingham | |
| 4,927,503 A | | 5/1990 | Polly | |
| 4,962,360 A | | 10/1990 | Homma | |
| 5,069,774 A | | 12/1991 | Hladky | |
| 5,071,526 A | * | 12/1991 | Pletcher et al. | 204/415 |
| 5,126,034 A | * | 6/1992 | Carter et al. | 204/403 |
| 5,173,166 A | * | 12/1992 | Tomantschger et al. | 204/412 |
| 5,221,893 A | | 6/1993 | Kondou | |
| 5,259,944 A | | 11/1993 | Feliu | |
| 5,323,429 A | | 6/1994 | Roarty | |
| 5,346,605 A | * | 9/1994 | Wolcott et al. | 204/415 |
| 5,369,370 A | | 11/1994 | Stratmann | |
| 5,370,776 A | | 12/1994 | Chen | |
| 5,519,330 A | | 5/1996 | Yamauchi | |
| 5,527,446 A | * | 6/1996 | Kosek et al. | 204/415 |

OTHER PUBLICATIONS

Corrosion Forms and Control for Infrastructure p. 154–169.

* cited by examiner

*Primary Examiner*—Jill Warden
(74) *Attorney, Agent, or Firm*—Streets & Steele; Jeffrey L. Streets; Frank J. Campigotto (57) ABSTRACT

An apparatus for electrochemical impedance spectroscopy having a solid electrolyte is disclosed. The apparatus has a chamber made of an electronically insulating material, a solid electrolyte coupled to the chamber and an electrode disposed in the chamber. A biasing member is used to urge the electrode towards the solid electrolyte and urge the solid electrolyte toward the substrate. The solid electrolyte is designed to contact the surface to be tested directly with no corrosive or otherwise harmful effect to the surface. A method for the detection of corrosion in bare or coated metallic substrates is also provided.

47 Claims, 10 Drawing Sheets

| | Damaged Area | Damaged Area/Probe Size |
|---|---|---|
| ◇ | 0 cm² | 0 % |
| □ | 5×10⁻⁴ | 0.0025 |
| △ | 5×10⁻³ | 0.025 |
| × | 5×10⁻² | 0.25 |
| ∗ | 5×10⁻¹ | 2.5 |

FIG. 4

Probe Contact Area
---------- 0.5 cm²
— — — 3.1
———— 20

Probe A (0.3 cm² CE sheet)

Probe B (20 cm² CE mesh)

Probe C (20 cm² CE sheet)

Failed test. Damaged site

Passed test

Intentionally damaged sites

Probe size

ELECTROCHEMICAL IMPEDANCE EVALUATION AND INSPECTION SENSOR

This invention was made with government support under contract F49620-95-C-0050 awarded by the Air Force. The government has certain rights in this invention.

BACKGROUND OF THE INVENTION

1. Field of the Invention

This invention relates to a nondestructive evaluation/inspection sensor and method for detection of corrosion in bared and painted metals and metallic alloys.

2. Background of the Related Art

Airline fleets operating for extended periods beyond their original design life-time depend on the ability to anticipate required adjustments in the inspection and maintenance activities to compensate for the aging aircraft. Aircraft metallic structures often suffer from corrosion during operation or storage, especially in humid, rainy, hot and seriously polluted areas. Corrosion may shorten the aircraft service life, increase maintenance costs, and cause structural failures. The development of inexpensive, practical, and user friendly nondestructive evaluation/inspection (NDE/I) techniques to detect corrosion with a high degree of accuracy, sensitivity and versatility is needed in the industry.

Aircraft metallic structures may suffer from corrosion even when they are covered with primers, coatings, and paint. Aircraft metallic structures can harbor deterioration that is un-detectable by visual inspection. Most of the NDE/I methods currently in use are based on detection principles which involve measurements of macroscopic changes in aircraft structures such as pits, crevices or cracks with sizable dimensions. These NDE/I techniques are not capable of detecting the early stages of corrosion initiation. Existing techniques also do not warn in advance of critical areas where possible severe corrosion could occur. In addition, existing NDE/I techniques for the detection of hidden corrosion present other practical limitations such as the need for highly trained personnel, cost, time, and the use of complicated and even hazardous instrumentation. Thus, the development of an inexpensive, user friendly, fast, and portable novel NDE/I system for the detection of hidden corrosion in aircraft structural components is highly desirable. Additionally, the new NDE/I system should be able to detect hidden corrosion in early stages so that both structural damage can be prevented and maintenance procedures can be minimized. Methods to both detect corrosion initiation of metallic structures and assess the amount and severity of damage to the metallic structures are critical to avoid failure of the structures and allow for the implementation of a systematic, cost effective approach to repairing and/or replacing damaged structures.

Corrosion of metallic structures is an electrochemical process per se, and several electrochemical techniques have been used in the past to detect and monitor corrosion of metals. One popular electrochemical technique for the detection and monitoring of corrosion is electrochemical impedance spectroscopy (EIS). This technique applies a small AC voltage perturbation across the substrate under study and measures the perturbation in the current response of the substrate. The impedance of the substrate (defined as the ratio between the applied potential and the measured current) is determined as a function of the frequency of the signal. The use of non-steady-state techniques with low amplitude perturbation signals (e.g., EIS) has become very attractive in corrosion research and testing, because it provides additional information on the kinetics of the corrosion process without significantly affecting the substrate under investigation. The majority of these techniques however, employ the use of liquid electrolytes. Liquid electrolytes (e.g., NaCl, $H_2SO_4$) typically damage the substrate being tested because of the presence of aggressive ions.

Painting and coating with organic polymer materials is a widely used method to provide corrosion protection to metallic substrates. The protective coating not only impedes the ingress of corrosive materials, but also decreases the electrical transport between anodic and cathodic sites on the metal surface. However, paint films are generally not impervious to reactants such as water, water vapor, oxygen and ions (e.g., chloride). The degradation of painted metals with time is characterized by many individual partial processes acting together, such as UV degradation, the permeation of water, oxygen and ions through the paint film, loss of color and gloss, changes in film adhesion with both degradation and wet/dry stages, and chemical degradation of the paint film. When the paint film is left deteriorated, corrosion of a base metal covered by the paint film finally causes flaking of the paint film and occurrence of rust. A non-destructive method for detecting corrosion even under painted surfaces would be very useful.

SUMMARY OF THE INVENTION

One embodiment of the present invention provides an apparatus for detecting corrosion. The apparatus has a chamber with an open end portion, a solid electrolyte, such as an ion exchange membrane, coupled over the open end portion of the chamber, and an electrode in electrochemical communication with the solid electrolyte. Preferably, the apparatus is self-contained leak-proof unit. A biasing member may be disposed in the chamber for biasing the electrode into contact with the electrolyte, and ultimately into contact with the substrate being tested. The open end portion of the chamber can be generally angular, stepped, concave, convex, or flat so that it may be adapted to fit the geometry of the substrate being tested. Preferably at least a portion of the chamber is made of an electronically and ionically insulating material. Preferably, the solid electrolyte is electronically insulating.

Preferably, an inert insulating member, such as PTFE (polytetrafluoroethylene) tape, is positioned between the biasing means and the electrode in order to protect the counter electrode from damage. The biasing means can be used to ensure that the electrode is in physical contact with the solid electrolyte. This is particularly important when a non-ionically conducting fluid is used to hydrate the solid electrolyte. In addition, the biasing member ensures sufficient contact between the solid electrolyte and the surface being tested.

The ion exchange membrane can be an ion exchange material selected from perfluorinated sulfonic acid polymers, perfluorinated carboxylic acid polymers, perfluoro bisulfonimide polymers, perfluoro phosphonic acid polymers, perfluorinated tetraalkylammonium salt polymers, carbanion acids, and mixtures thereof. It is preferred that the solid electrolyte has a charge carrier comprising a non-corrosive ion, such as a cation or an anion. A current conductor may be attached to the electrode. The solid electrolyte can have an area of from about 0.1 $cm^2$ to about 10,000 $cm^2$, preferably, from about 1.8 $cm^2$ to about 154 $cm^2$.

In a preferred embodiment, the chamber has an inside surface defining a cavity and a support means positioned within the cavity. The support means defines a bore extending therethrough that is in flow communication with the solid electrolyte. The bore is preferably at least partially filled with fluid, such as water or a liquid electrolyte. The biasing member is positioned between the support means and the electrode and defines a bore therethrough that is in axial alignment with the bore defined by the support means.

The electrode used in the apparatus, may be made from a material selected from platinum, a platinum group metal, gold, a gold group metal, iridium, rhodium, ruthenium, tungsten, titanium, zirconium, stainless steel, carbon, conductive oxides, such as a platinum oxide or oxide forms of a platinum group metal, gold oxides, oxide forms of gold group metals, iridium oxide, rhodium oxide, ruthenium oxide, tungsten oxide, tin oxide, or mixtures thereof. Alternatively, the electrode may be made from a material coated with platinum, a platinum group metal, gold, a gold group metal, iridium, rhodium, ruthenium, tungsten, titanium, zirconium, stainless steel, carbon, conductive oxides, such as a platinum oxide or oxide forms of a platinum group metal, gold oxides, oxide forms of gold group metals, iridium oxide, rhodium oxide, ruthenium oxide, tungsten oxide, tin oxide, or mixtures thereof. The material can be in the form of metal sheets, metal gauze, thin film electrodes, and porous electrodes.

In another embodiment, there is provides a method for detecting corrosion in metallic substrates. The method includes positioning an electronically insulating ionically conducting member in electrochemical communication between a substrate to be inspected and an electrode, applying an AC signal across the electrode and the substrate, and determining an impedance reference value for the substrate. In addition, the impedance value between the substrate and the electrode is also determined. Preferably, the electronically insulating ionically conducting member is a non-corrosive, ion exchange membrane. The surface of the substrate to be tested is preferably moisturized with a non-corrosive liquid such as water, prior to contacting the apparatus with the substrate.

Preferably, a voltage is applied at a selected frequency and an average impedance value is obtained. The impedance reference value is compared with the average impedance value and whether the substrate contains corrosion is determined based on the comparison between the impedance reference value and the average impedance value.

The present invention also provides an apparatus for analyzing corrosion having a solid electrolyte, an electrode in electrochemical communication with the solid electrolyte and a source of a fluid for hydrating the solid electrolyte. The solid electrolyte can be made of an electronically insulating, ionically conducting material, preferably containing a non-corrosive ion. An impedance measuring element may be positioned in electrical contact with the electrode. The source of fluid may be a chamber in fluid communication with the solid electrolyte.

Another embodiment of the present invention provides an apparatus for analyzing corrosion having a sensor having a solid electrolyte, an electrode in electrochemical communication with the solid electrolyte, and a source of a fluid for hydrating the solid electrolyte; and an impedance measuring element in electrical contact with the electrode. The solid electrolyte can be made of an electronically insulating, ionically conducting material, containing a non-corrosive ion, as discussed previously. The impedance measuring element is preferably adapted to generate an AC signal at a selected frequency, measure the perturbed signal, and calculate the corresponding impedance of a substrate being tested. The source of fluid can be a chamber in fluid communication with the solid electrolyte, preferably at least a portion of the chamber is made of an electronically and ionically insulating material.

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present invention provides a non-destructive evaluation/inspection (NDE/I) sensor for detecting the early stages of corrosion in metallic structures based on electrochemical impedance measurements. The sensor utilizes an ionically conducting membrane disposed between a counter electrode and a metal or metallic alloy substrate to be tested for corrosion. Electrochemical impedance is measured when applying a small AC signal perturbation between the substrate and the counter electrode.

In one aspect of the invention, a sensor may be constructed from a chamber or housing, preferably made of an electronically and ionically insulating material. The chamber has an open end portion with a solid electrolyte or other ionically conducting material coupled over the open end portion. A counter electrode is disposed in electrochemical communication with the solid electrolyte. In one embodiment, the sensor may include a biasing member disposed to urge the electrode towards the solid electrolyte and urge the solid electrolyte toward the substrate being tested. Alternatively, the counter electrode may be fixed to the solid electrolyte. The counter electrode in this instance could be a thin film electrode, sometimes referred to as an ink electrode, or the counter electrode may be fixed to the said electrolyte by hot pressing. The counter electrode is in electrical communication with an instrument for measuring electrochemical impedance. The chamber is preferably sealed to contain a fluid so that no fluid such as water, is released from the chamber or the solid electrolyte but provides fluid such as water to the solid electrolyte to support ion conduction.

The counter electrode may be made from platinum, a platinum group metal, gold, a gold group metal, iridium, rhodium, ruthenium, tungsten, titanium, zirconium, stainless steel, carbon, conductive oxides, such as a platinum oxide or oxide forms of a platinum group metal, gold oxides, oxide forms of gold group metals, iridium oxide, rhodium oxide, ruthenium oxide, tungsten oxide, tin oxide, or mixtures thereof. In addition, a metal or material coated with any of the materials listed above could also be used as a counter electrode, as well as any of the materials listed above on a carbon-based support.

The electronically insulating, ion exchange membrane can be either a cation exchange membrane or an anion exchange membrane. Cation exchange membranes may be made of a polymer material having sulfonate functional groups contained on a fluorinated carbon backbone. Such materials include NAFION® membranes (NAFION® is a registered trademark of E.I.DuPont de Nemours and Co., Wilmington, Del.) having an equivalent weight of 1100 (NAFION® 115 and NAFION® 117) and 1000 (NAFION® 105) and a Dow proton exchange membrane (XUS-13204.20) having an equivalent weight of 800 grams. In addition, it is anticipated that a sulfonated polymer having a nonfluorinated carbon backbone would be operable according to the present invention. Such a polymer might include polystyrene sulfonate. It is also anticipated that cation exchange membranes made of a polymer material having carboxylate functional groups attached to a fluorinated carbon backbone would be operable according to the present invention. Examples include those available from Tokuyama Soda Company under the trademark "NEOSEPT-F", Asahi Glass Company under the trademark "FLEMION", Asahi Chemical Industry Company under the trademark "ACIPLEX-S", and Tosoh Corporation under the trademark "TOSFLEX IE-SA48". Further, polymeric systems based on perfluoro bis-sulfonimides, perfluoro phosphonic acids, and the corresponding carbanion acids would function satisfactorily according to the present invention.

The preferred cation exchange membranes contain perfluorinated sulphonic acid and display a very high resistance to chemical attack, such as NAFION® 117, NAFION® 115, and NAFION® 105. NAFION® 105 is the most preferred membrane, because it exhibits lower electronic resistance at room temperature.

The charge carrier used in the cation exchange membranes described herein are preferably non-aggressive ions, most preferably, sodium ions. The protons present on the acid form of the ion exchange membrane can easily be substituted with sodium ions by soaking the ion exchange membrane in a NaOH solution for a period of time, such as a 30% aqueous NaOH solution for one day, then rinsing with deionized water.

Anion exchange membranes, such as the membranes provided by Tokuyama Soda, Co., Ltd. (e.g., Neosepta), Electrosynthesis Company, and Asahi Glass (e.g., Selemion DSV), can be used as the electronically insulating, ionically conducting solid material. The charge carrier should not be aggressive toward corrosion. Some examples of suitable anion charge carriers include formate and acetate. Membranes using chloride ions as carriers should be avoided due to their corrosive nature.

The sensor is used to measure the electrochemical impedance of the interface of a particular substrate. The electrochemical impedance is measured by applying a small AC voltage perturbation (dV) across the substrate under study and measuring the perturbation in the current response (dI). Alternatively, a small AC current perturbation (dI) may be applied across the substrate and the resulting perturbation in the voltage (dV) is measured. A voltage source has a first terminal in electronic communication with a counter electrode in contact with the solid electrolyte, which is in physical contact with the substrate being tested and a second terminal in electronic communication with the substrate. The impedance of the substrate (i.e., dV/dI) is determined as a function of the frequency of the signal (e.g., from 32 MHz to 10 $\mu$Hz, typically between 20 kHz and 0.1 Hz).

Although scanning the signal in a wide frequency range contains a lot of information about the substrate under study, it has been found that changes due to the corrosion process can be identified at a single frequency or in a small number of frequencies. Using a single frequency or only a few frequencies where the impedance signal is very sensitive to the corrosion stage of the substrate substantially reduces the time required for data acquisition and analysis, which can be time consuming if frequencies are scanned over a wide range (e.g., from KHz to mHz). In addition, data analysis is simplified: instead of using equivalent circuits and mathematical models to interpret the role of corrosion, data acquisition at a single frequency or few frequencies only requires the comparison with a reference point which can be carried out once and stored in the memory of a microprocessor. Another advantage of using only a few frequencies is that the electronics to control and analyze the signal are simplified.

The sensor can use a single or a small number of characteristic frequencies of the AC signal applied between the sensor and the structure under test. The use of a single frequency provides real time response and fast evaluation of the substrate corrosion status. Real time evaluation of the corrosion process is easily achieved because the impedance signals at the selected frequencies are highly sensitive to corroded or damaged areas of a substrate.

In order to obtain the impedance measurements it is essential to have a counter electrode and a ion conducting membrane, such as a solid electrolyte membrane between the counter electrode and the surface being tested. The chamber is not necessary, however, the role of the chamber is: (i) as a support, to maintain the integrity of the counter electrode/membrane assembly; (ii) to provide the humidity that the membrane needs, and (iii) to provide the mechanism that permits a good contact between the membrane and the substrate without damaging the membrane. It is necessary that the impedance measurement be limited to the counter electrode/membrane/substrate interfaces. If there is an additional metal contact, the impedance measurements will include the additional metal as well as the substrate being tested. In addition, certain metals, such as aluminum, will exchange metal ions ($Al^{+3}$) with the membrane, therefore changing the conductivity of the membrane and ultimately giving irreproducible results. Therefore, if a chamber is used, the portion of the chamber that is in direct contact with the solid electrolyte or the counter electrode should be made of an ionically and electronically insulating material and the remaining portion of the chamber may be made of any material. Alternatively, an ionically and electronically insulating gasket can be placed between the chamber and the solid electrolyte and between the chamber and the electrode. In addition, an electronically conductive chamber that is in electrical communication with the electrode can be used as the current collector.

Figure 1:
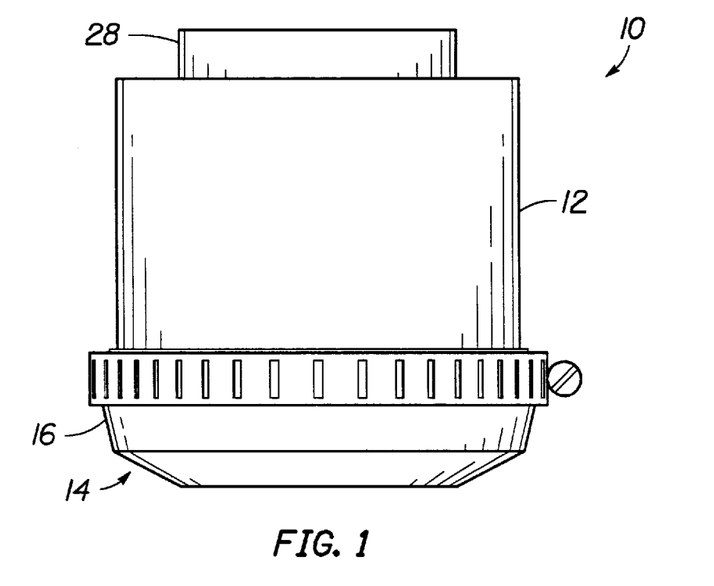
FIG. 1 is a side view of a sensor in accordance with the present invention.
Figure 1A:
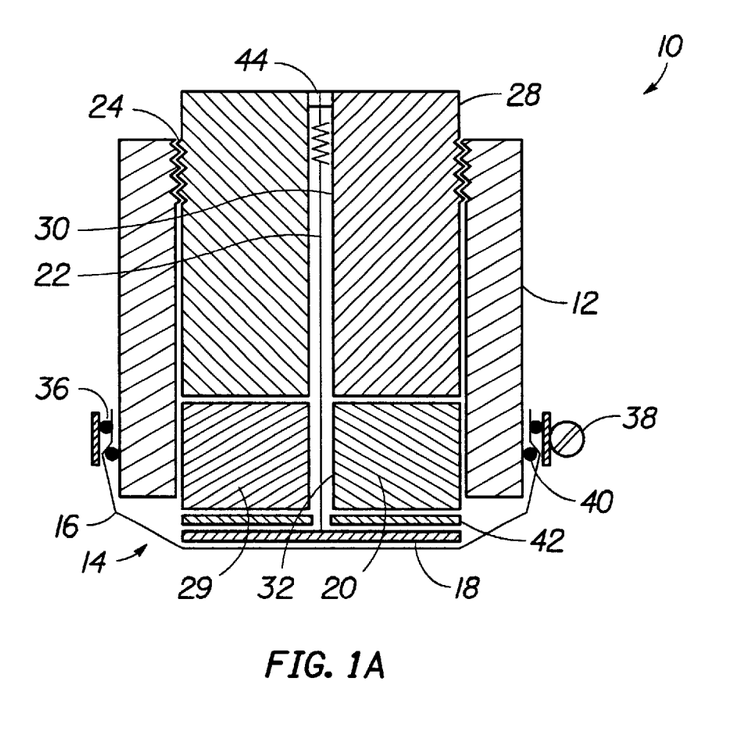
FIG. 1A is a cross-sectional side view of the sensor of FIG. 1.

Referring to FIGS. 1 and 1A, the sensor 10 has a chamber or housing 12 with an open end portion 14. The chamber 12 is made of an electronically insulating and ionically insulating material such as polyethylene. A solid electrolyte 16 is coupled over the open end portion 14 of the chamber 12. An electrode 18 is disposed in the chamber 12 in electrochemical communication with the solid electrolyte 16. A biasing member 20 is disposed in the chamber 12 to urge the electrode 18 towards the solid electrolyte 16 and urge the solid electrolyte 16 toward the substrate 46 (See FIGS. 2 and 2A). The biasing member 20 may be secured in position by a support member 28 such as a polyethylene body, and the biasing member 20 may be a spring or a compressable material. The support member 28 defines a bore or chamber 30 of various sizes and shapes therethrough. The biasing member 20 also defines a bore 32 that is in coaxial alignment with the bore 30. The bores 30, 32 provide a small chamber in fluid communication with the solid electrolyte 16, wherein the small chamber can be partially or fully filled with fluid such as water for keeping the solid electrolyte 16 in a saturated state. Alternatively, the bore may be filled with a liquid electrolyte, such as sodium sulfate, to provide ionic contact between the counter electrode and the solid electrolyte 16. Optionally, an inert insulating member 42, such as a piece of polytetrafluoroethylene (PTFE) sealant tape, may be positioned between the biasing member 20 and the electrode 18 to protect the electrode 18 from physical damage.

Alternatively, the counter electrode 18 may be fixed to the electrolyte 16. The counter electrode 18 in this instance could be a thin film electrode, sometimes referred to as an ink electrode, or the counter electrode 18 may be fixed to the electrolyte 16 by hot pressing.

The chamber 12 is preferably completely sealed so that essentially no fluid escapes from the sensor 10. Thus, the sensor 10 can be used for the inspection of surfaces at any position, such as the sensor positioned against a substrate's top, bottom, side or angled surface. One way to seal the solid electrolyte 16 to the chamber 12 is with the aid of a first o-ring 36, a second o-ring 40 and a clamping member, such as a worm drive hose clamp 38 positioned around the solid electrolyte 16 and the o-rings 36, 40. The bore 30 through the support member 28 is also preferably sealed with a cap 44. The cap can be removed to fill the bores 30 and 32 with fluid for hydrating the solid electrolyte. Therefore, while the sensor 10 is completely self-contained, the insulating member 42 and the biasing member 20 bias the electrode 18 and in turn the solid electrolyte 16 toward a substrate 46 to be tested, (See FIGS. 2 and 2A), providing void-free contact between the sensor 10 and substrate 46.

The counter electrode 18 is preferably made of a stable metal, most preferably platinum, a platinum group metal, or a metal coated with a platinum group metal. The counter electrode 18 can be made from metal sheet, metal gauze, thin film electrodes (including ink electrodes), or porous electrodes. A preferred counter electrode 18 is made of a platinum gauze of 52 mesh woven from 0.1 mm diameter wire.

The counter electrode 18 is coupled to a power source by a conducting wire 22. The conducting wire 22 may be located in the chamber 12, preferably, passing through the bores 30 and 32, and the insulating member 42. The conducting wire 22 is preferably flexible and can be compacted or stretched during inspection of a particular substrate to accommodate for movement of the counter electrode in response to the surface of the test substrate.

The solid electrolyte 16, is an electronically insulating, ionically conducting electrolyte. In one example of the present invention, a NAFION® 105 membrane, was used after being soaked in 30% NaOH for 1 day to replace the major charge carrier from $H^+$ to $Na^+$. The membrane was kept wet to sustain a high conductivity by adding a few drops of water to the bore 30 of the support means 28. $Na^+$ are preferred due to their non-corrosive nature.

Figure 2:
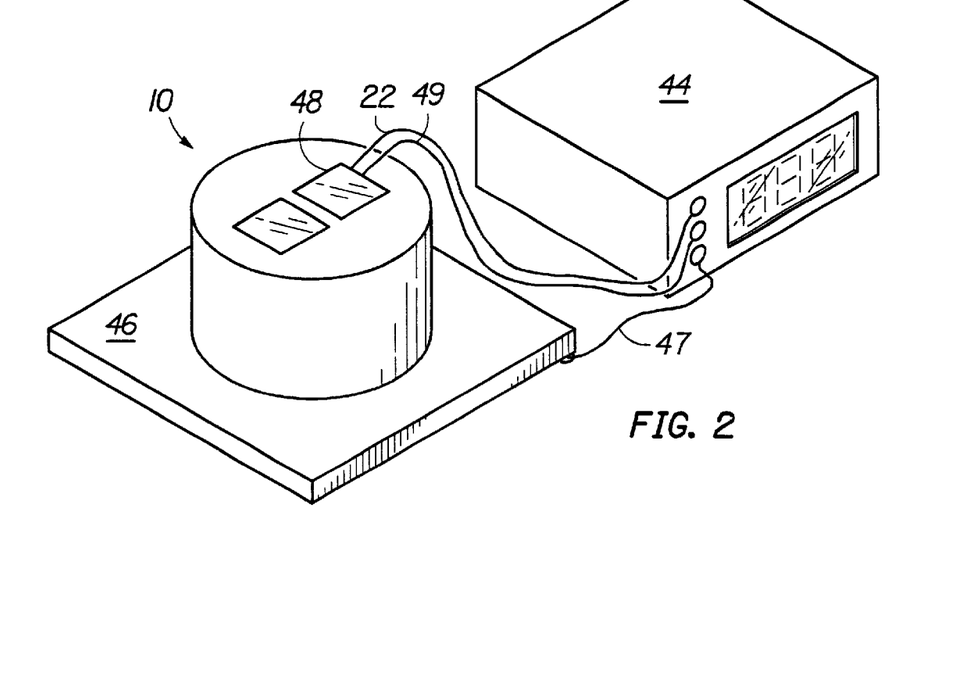
FIG. 2 is a schematic diagram of the sensor being used to measure corrosion on a substrate.

Referring to FIG. 2, the sensor 10 is connected via the conducting wire 22, to an instrument 45, which consists of a potentiostat interfaced with any of the following instruments: a frequency response analyzer, an impedance/gain phase analyzer, such as a Solartron 1260, a lock-in amplifier, or a custom designed electronic instrument, which generates an AC signal (either current or voltage) at a selected frequency and measures the perturbed signal (either voltage or current), and calculates the corresponding impedance of a substrate 46 being tested. The instrument 44 is also connected to the substrate 46 by an electronically conductive wire 47. The sensor 10 preferably has a display 48 connected to the instrument 44 in a line 49, that shows the measured impedance or displays "pass or failed test" signals (e.g., green light for a passed test, i.e., no corrosion, and red light for a failed test, i.e., corroded) if the measured impedance is compared to a stored reference impedance value which indicates the threshold value of the impedance signal below which the substrate 46 is corroded. At a given frequency, the value of the impedance amplitude of a defect free coating is higher than the impedance amplitude of a coating having defects.

The basic design for the display 48 may be as simple as providing two small light bulbs or LEDs, preferably one green and one red. Depending on the impedance signal from a region of the substrate, the microprocessor will recognize the substrate as "good" or as "corroded". For the "good" substrate, the microprocessor will send an electronic signal, such that the green light will be turned on. On the other hand, if a corroded region of the substrate is detected, the microprocessor will send another electronic signal, such that the red light will be turned on. Optionally, the display 48 may be a stand alone display or built into either the sensor 10 or the instrument 44. Preferably, the display 48 is in the instrument 44, to simplify the design for the sensor 10 and require only one display for multiple sensors.

Two connections are needed from the instrument 44 in order to measure the impedance: one to the sensor 10, and another to the substrate 46. Another option is to have a cordless system (similar to the one used in telephones), where a signal will be sent from the instrument 44, and received by the sensor 10, and then a signal will be sent from the sensor 10, and received by the instrument 44.

The microprocessor can be either in the instrument 44 or in the sensor 10, preferably in the instrument 44, so that the design of the sensor 10 will be much simpler and only one microprocessor will be needed despite the use of multiple probes. On the other hand, having the microprocessor in the sensor 10 would require a microprocessor in each sensor.

Figure 2A:
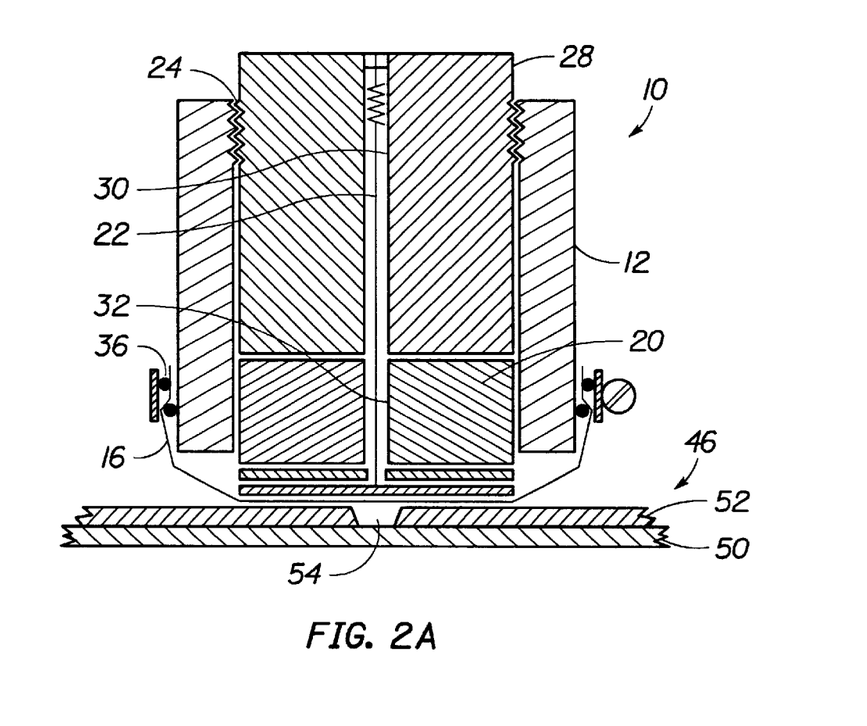
FIG. 2A is a cross-sectional side view of the sensor and substrate of FIG. 2.

Referring to FIG. 2A, the sensor 10 is shown in cross-section, positioned over a substrate 46 having a corroded site 54. In the case of a metal substrate, typically the surface of the metal is covered with a protective film 52, such as oxide or paint, that is electronically insulating. When the film 52 is damaged, corrosive elements, such as air or water, are allowed to come in contact with the surface of the substrate and eventually corrode the substrate. By providing water onto the surface of the substrate 46, during EIS measurement, an ionically conductive pathway is established between the solid electrolyte 16 and the highly conductive portion of the metal or metallic alloy substrate which underlies the film 52 or other corroded regions. Site 54 can be as small as a pinhole, e.g. a few micrometers wide.

EXAMPLE 1

Figure 3:
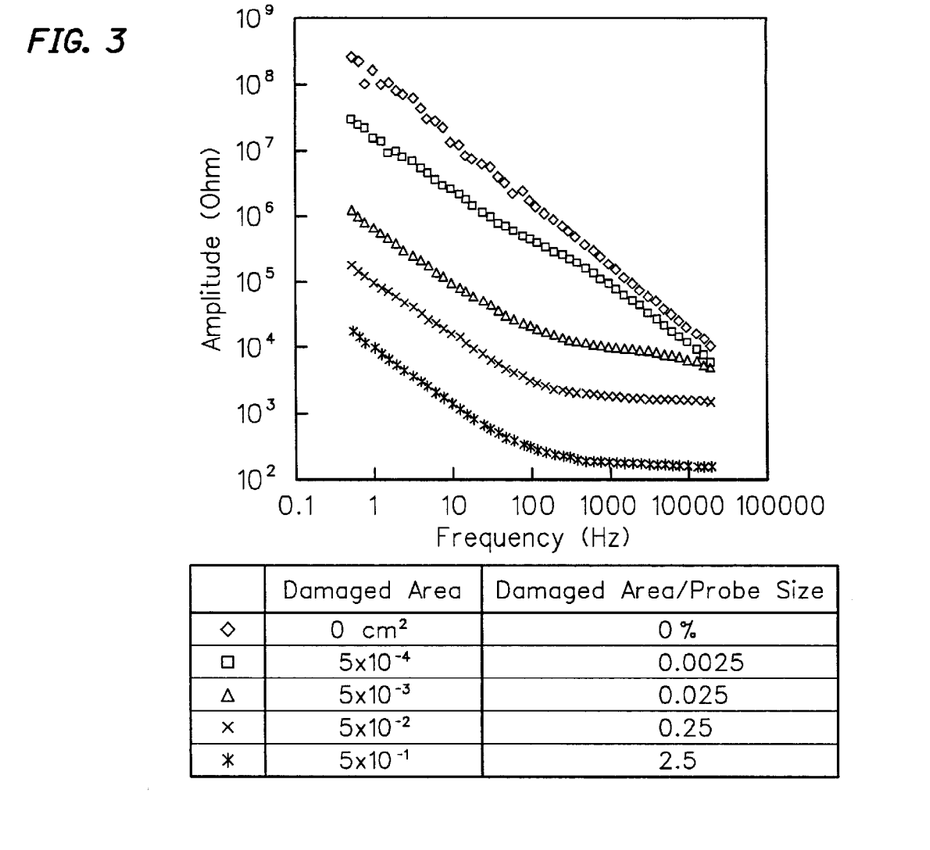
FIG. 3 is a chart showing the variation of impedance amplitude with frequency for a painted Alclad 7075-T6 coupon with different degrees of damage detected with a sensor of 20 cm$^2$.

FIG. 3 shows the impedance amplitude measured by a Solartron 1260 Impedance/Gain Phase analyzer interfaced with an EG&G PAR Potentiostat/Galvanostat Model 1273, of painted Alclad 7075-T6 coupons containing flaws of different sizes measured with the sensor 10 using a Nafion membrane as the solid electrolyte, having an active surface area of 20 $cm^2$. Impedance signals were recorded as a function of the AC frequency, when a 50 mV voltage was applied. The paint film consisted of a primer and top coat according to MIL-P-23377 and MIL-C-83286, respectively. Flaws were made by scribing the paint film to expose the metallic substrate. The flaw area was measured by means of an optical microscope. The spectrum (i.e., impedance amplitude vs. frequency) of a coupon with no flaw is also included. The smallest damaged area detected was $5 \times 10^{-4}$ $cm^2$. (i.e., a pinhole of 126 $\mu$m in diameter). In this example, the smallest ratio of the damaged area to the sensor size was 0.0025%. This is a remarkable result that shows the high sensitivity of the sensor of this invention to detect areas prone to corrosion.

Figure 4:
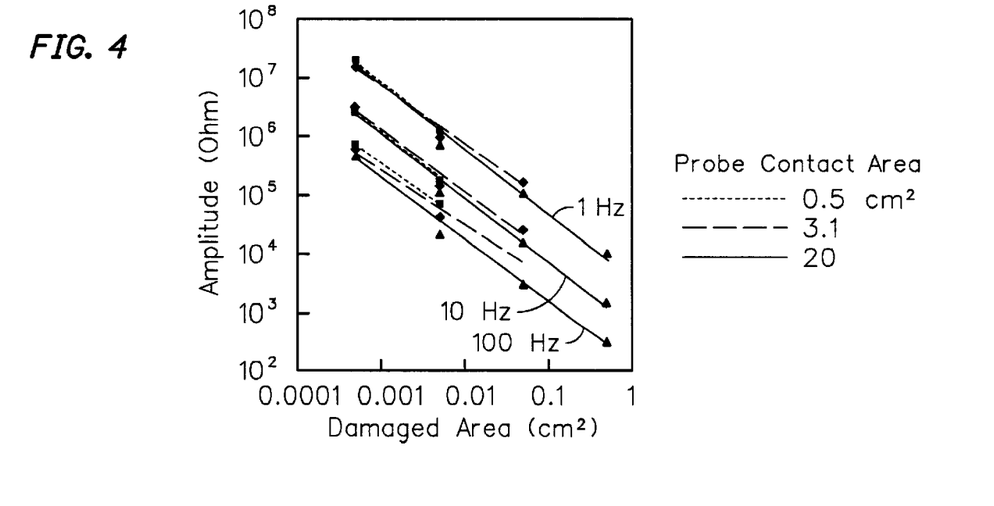
FIG. 4 is a chart showing the variation of impedance amplitude with the damaged area on a painted Alclad 7075-T6 coupon measured at three different frequencies and using three different sensor sizes.

FIG. 4 shows the impedance amplitude vs. the area of the flaws detected at three frequencies with three different sensor sizes (0.5, 3.1 and 20 $cm^2$). It can be observed that: (i) for a given damaged area, the impedance amplitude is dependent on the frequency; (ii) for a given frequency there is a linear relationship between the log of amplitude with the log of the damaged area; (iii) the relationship is independent of the sensor size at 1 and 10 Hz; (iv) the relationship is dependent on the sensor size at 100 Hz (i.e., the impedance magnitude at 100 Hz contains information on the sensor size); and (v) it is possible to detect a range of damaged areas of more than three orders of magnitude without compromising the resolution of the signal. Three very important conclusions can be obtained from this example. First, at a fixed frequency value, the value of the impedance magnitude (i.e. absolute value) drastically decreases in the presence of a damaged area with respect to the value obtained for a surface with no flaws. This change can be of several orders of magnitude, depending on the flaw size. In the presence of a flaw, the impedance amplitude is mainly determined by the presence of flaws. In the absence of a flaw, the impedance amplitude is determined by the resistive properties of the surface (e.g., coating or film) and the area under test. Second, the magnitude of the impedance signal is independent of the size of the sensor at selected frequencies. This allows the use of relatively big sensor sizes for scanning large areas. Once a problematic area is detected, smaller sensors are preferably used to further localize the corroded site. This significantly reduces the cost and time of the inspection. Third, a single frequency, or at most, a few frequencies, can be used to measure the magnitude of the impedance signal and obtain valuable information on the corrosion state of an inspected sample. This significantly simplifies the impedance analyzer instrument and reduces the time required for inspection and data interpretation, so that real time inspections can be performed. For example, to obtain an impedance spectrum from 0.5 Hz to 20 KHz may take from 3 to 5 minutes. On the other hand, to obtain 10 readings at 10 Hz and to calculate the average value takes less than 5 s. Using a microchip in either the sensor or the instrument, this average value can be compared with the value of a reference point stored in the memory, so that it can be instantly determined if the tested area contains a problematic area or not.

EXAMPLE 2

Figure 5:
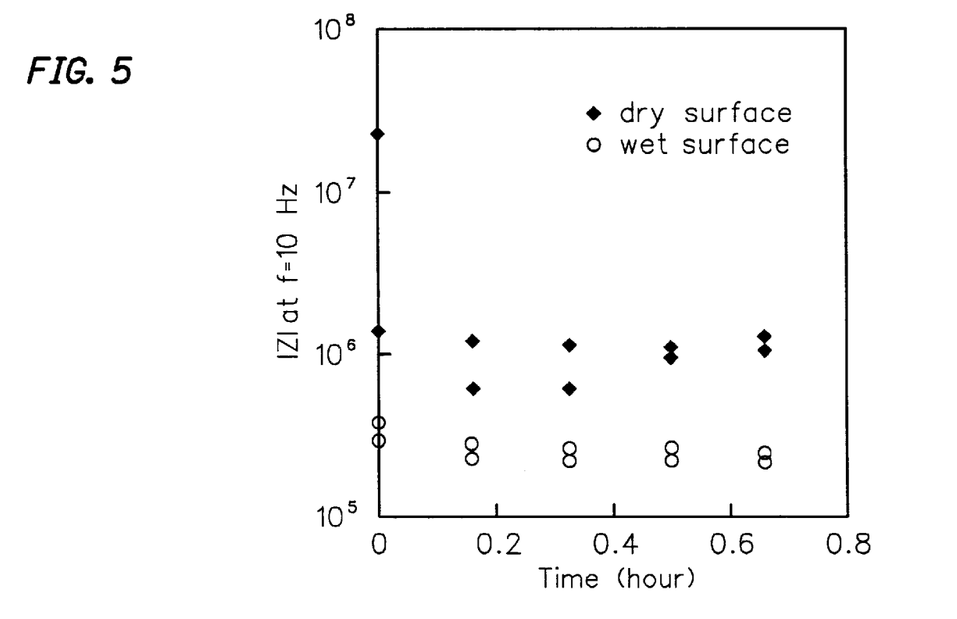
FIG. 5 is a chart showing the variation of impedance amplitude measured by a 20 cm$^2$ sensor at 10 Hz over a period of time in the presence, and in the absence, of a water film on a painted Alclad 2024-T3 coupon containing a flaw of $5\times10^{-3}$ cm$^2$.

FIG. 5 shows the effect of the presence of a water film on the magnitude of the impedance signal at 10 Hz when a 50 mV voltage was applied from a painted Alclad 2024-T3 coupon with a flaw of $5-10^{-3}$ $cm^2$. In this case, the sensor 10 (20 $cm^2$) was removed from the surface of the coupon after each test. For the wet conditions, water was added (2–3 drops) before each test. It is clear that the presence of water on the coupon surface played an important role during the test since when water was present, reproducible results were obtained. However, when the coupon was tested under dry conditions, the results were scattered and irreproducible. Unless otherwise indicated, in the experiments described here, the surface was wetted with water before each inspection was carried out with the sensor of this invention. The water creates a conductive layer between the solid electrolyte and the substrate.

Figure 6:
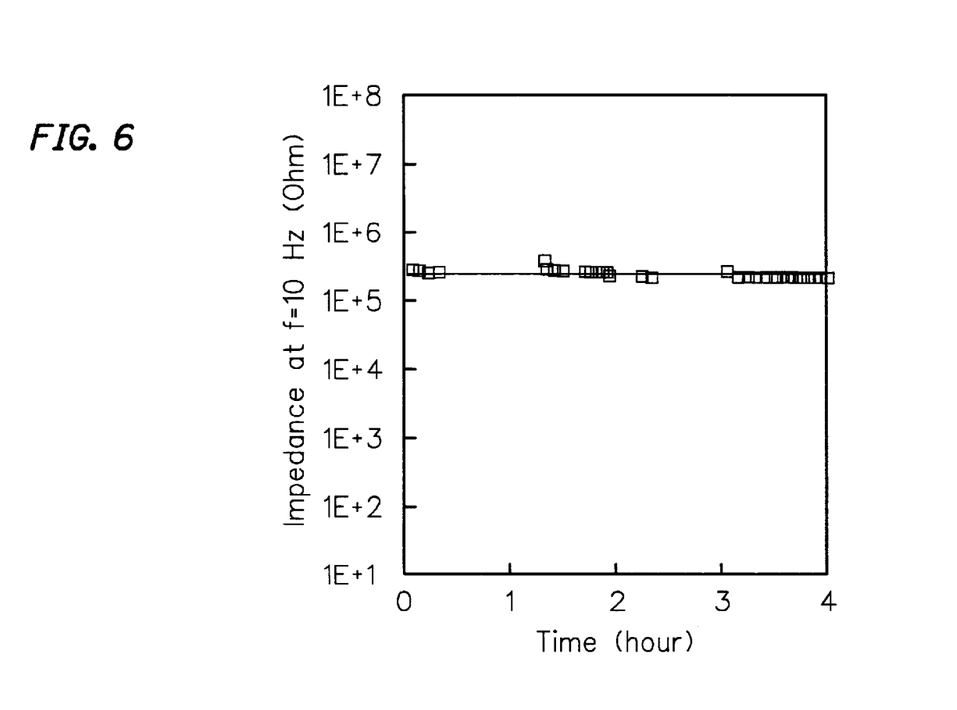
FIG. 6 is a chart showing the variation of the impedance magnitude measured by a 20 cm$^2$ sensor at 10 Hz over a period of time for a painted Alclad 2024-T3 coupon containing a flaw of $5\times10^{-3}$ cm$^2$.

FIG. 6 shows the magnitude of the impedance signal measured by the sensor 10 (20 $cm^2$) using a 10 Hz, 50 mV signal on a painted Alclad 2024-T3 coupon with a flaw of $5 \times 10^{-3}$ $cm^2$. The signal was recorded over a period of four hours. Before each test, the surface was moistened with water (2–3 drops) and then the sensor was placed on the top of the flaw. It can be observed that the impedance signal remained at about the same value during the entire time of the test.

Figure 7:
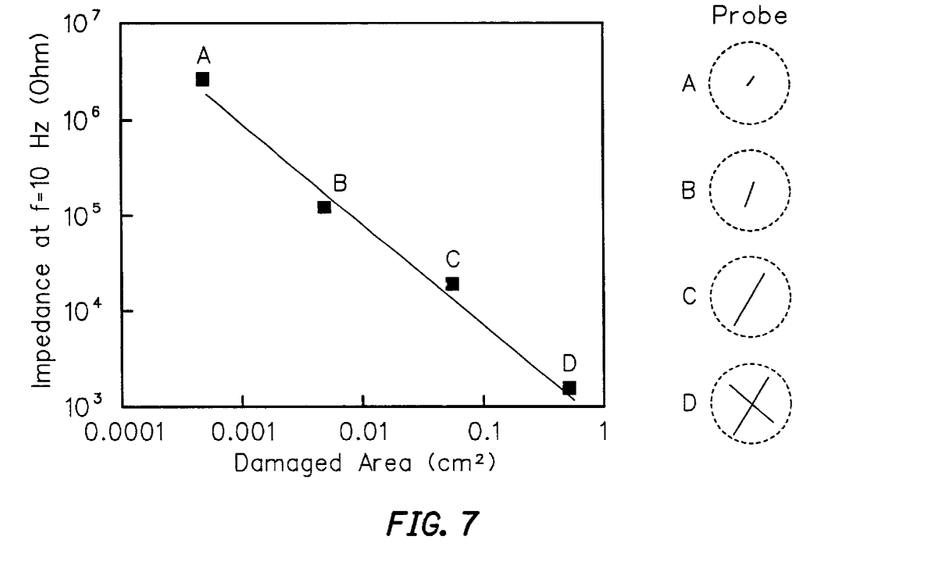
FIG. 7 is a chart showing the variation of the impedance magnitude measured by a 20 cm$^2$ sensor at 10 Hz of damaged areas on a painted Alclad 2024-T3 coupon.

To study the sensitivity and resolution of the sensor of the present invention, painted Alclad 2024-T3 coupons with different flaw areas were tested. FIG. 7 shows the impedance magnitude as a function of the flaw area when a signal of 10 Hz and a voltage of 50 mV was used. It can be observed that there is a linear relationship between the logarithm of the impedance magnitude with the logarithm of damaged area. The impedance signal was found to be independent of the shape of the damaged area or the number of discrete damaged areas (e.g., multiple small flaws or few bigger flaws), as long as the total damaged area was constant.

EXAMPLE 3

Figure 8:
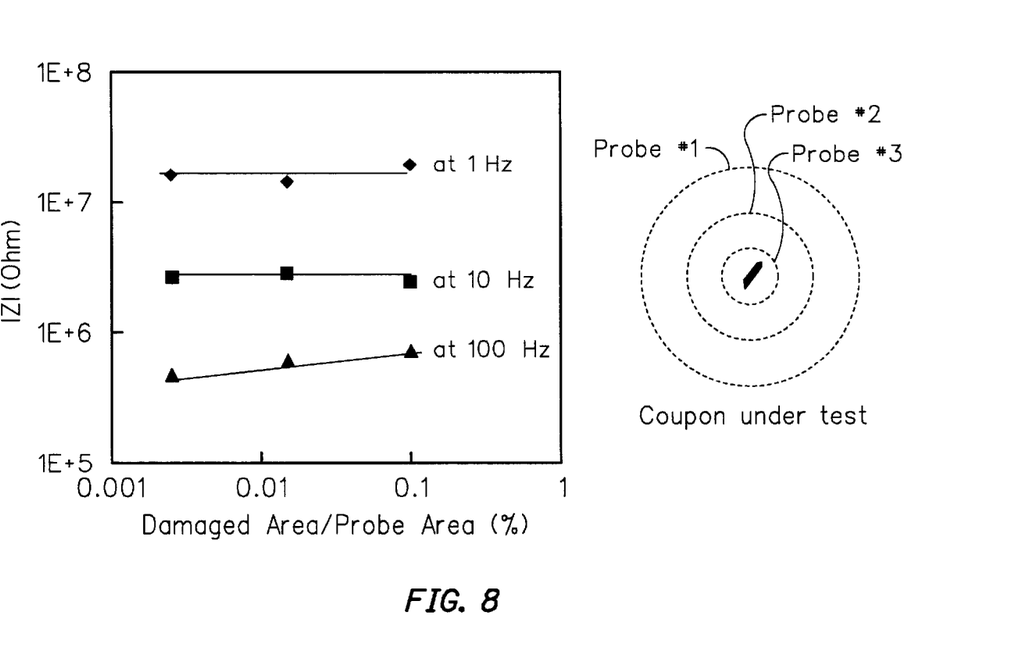
FIG. 8 is a chart showing the variation of the impedance magnitude with the ratio of flaw size to sensor area at three different frequencies (1, 10 and 100 Hz) of a painted Alclad 7075-T6 coupon. The area of the flaw was kept constant at $5\times10^{-4}$ cm$^2$ and three different sensor sizes were used (0.5, 3.1 and 20 cm$^2$).

FIG. 8 shows the magnitude of the impedance signal as a function of the ratio of the flaw area to sensor area at three different frequencies (1, 10 and 100 Hz) when a 50 mV voltage was applied. In this experiment, a single flaw with an area of $5 \times 10^{-4}$ cm$^2$ was tested with sensors having different membrane areas (0.5, 3.1 and 20 cm$^2$). At frequencies of 1 and 10 Hz there was no apparent effect of the sensor size. On the other hand, the impedance signal recorded at 100 Hz showed a certain dependence on the sensor size. This example also shows the high sensitivity of the present invention to detected areas prone to corrosion. The minimum ratio of the damaged area to sensor area that could be detected in the present example was about 0.0025%. In another experiment, a flaw with an area of $5 \times 10^{-4}$ cm$^2$ was detected with a sensor of 154 cm$^2$. In this case, the ratio is about 0.0004%. This extremely low ratio allows the inspection of large surface areas with relatively large sensors. Once a damaged or corroded area is detected, the surface will be further inspected with sensors of smaller size to localize the corroded site.

Figure 9:
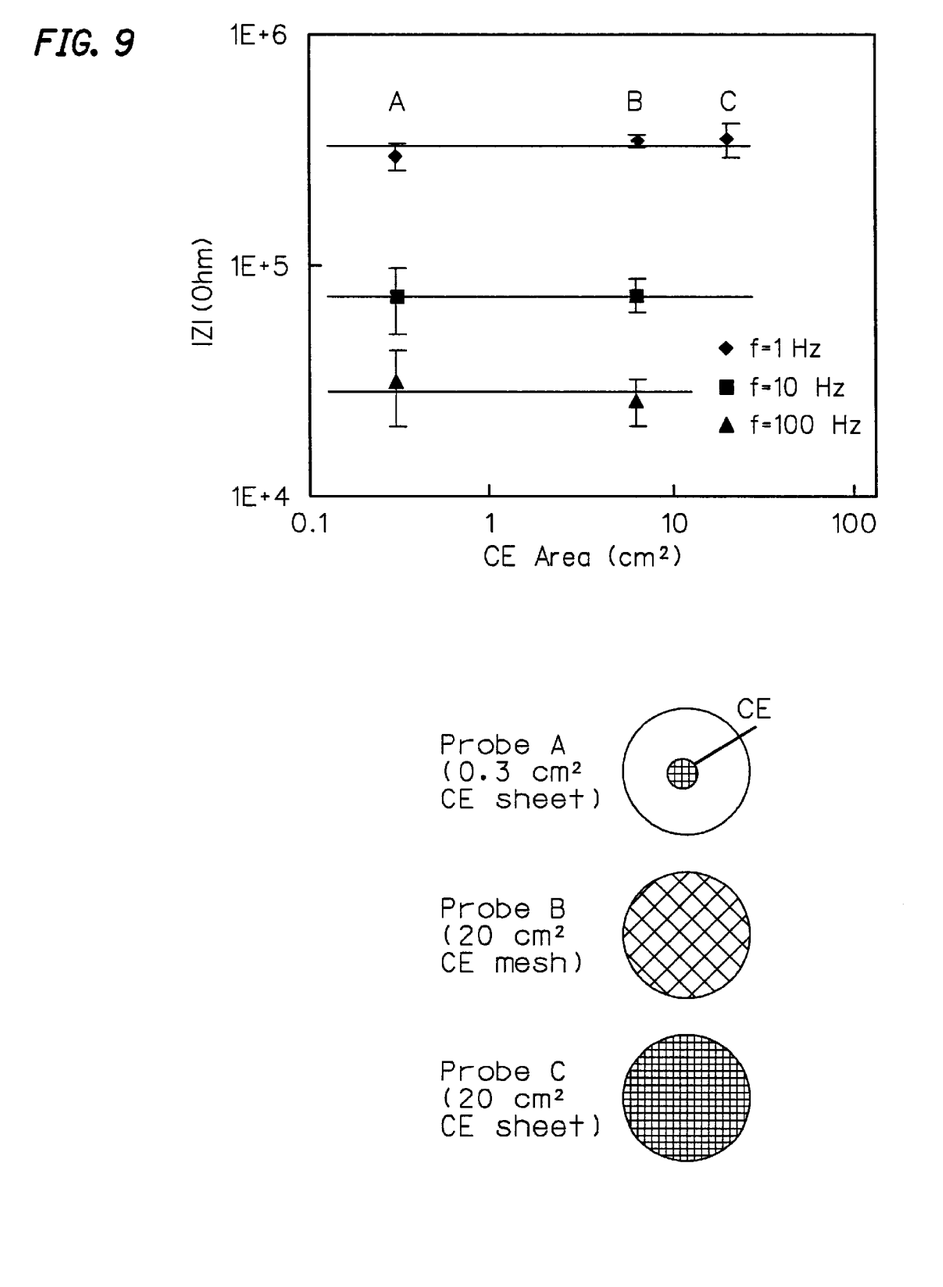
FIG. 9 is a chart showing the variation of the impedance magnitude with the size of the counter electrode on a painted Alclad 7075-T6 coupon measured at three different frequencies (1, 10 and 100 Hz). The area of the flaw was $5\times10^{-3}$ cm$^2$ and the area of the sensor was 20 cm$^2$.

An important component of the sensor is the counter electrode 18, shown in FIGS. 1 and 1A. Prototype sensors were constructed using counter electrodes made of Pt having different areas, shapes and configurations (e.g., disc and mesh). FIG. 9 shows that at 1 Hz and 10 Hz, the magnitude of the impedance signal when 50 mV was applied, was independent of the counter electrode 18 size and shape. Thus, at selected frequencies, the information contained in the impedance magnitude is dependent on the test sample, and not on the counter electrode 18. This finding substantially simplifies the design of the sensor, and allows the use of a reference point (independent of the counter electrode size and geometry) indicative of a non-corroded substrate for use of the EI-NDE/I sensor.

EXAMPLE 4

Figure 10:
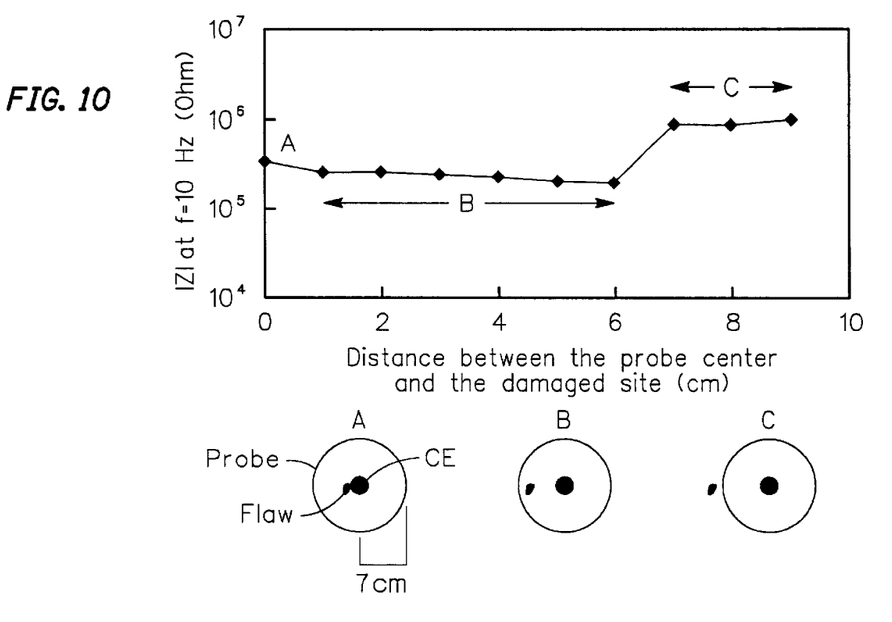
FIG. 10 is a chart showing the variation of the impedance magnitude as a function of the distance between the center of the sensor and the flaw on a painted Al7075-T6 coupon measured at 10 Hz. The area of the sensor was 154 cm$^2$, and the area of the counter electrode was 0.3 cm$^2$.

This example shows that the relative position between the counter electrode and the damaged area does not substantially affect the detection of the damaged area as long as the damaged area is within the area under test (i.e., in electrochemical communication) with the sensor 10. FIG. 10 shows the results obtained using a sensor having a 154 cm$^2$ area, with a counter electrode of 0.3 cm$^2$ located in the middle of the sensor 10. The test coupon was a painted Alclad 7075-T6 with a flaw of $1 \times 10^{-3}$ cm$^2$. It was found that, as long as the flaw is located within the area in contact with the sensor, the signal is independent of the distance between the electrode and the flaw. Once the flaw is outside the contact area tested by the sensor 10, the impedance magnitude corresponded to the value of a flaw-free surface. Thus, during inspection, there is no interference from flaws existing outside the area being inspected.

EXAMPLE 5

Figure 11:
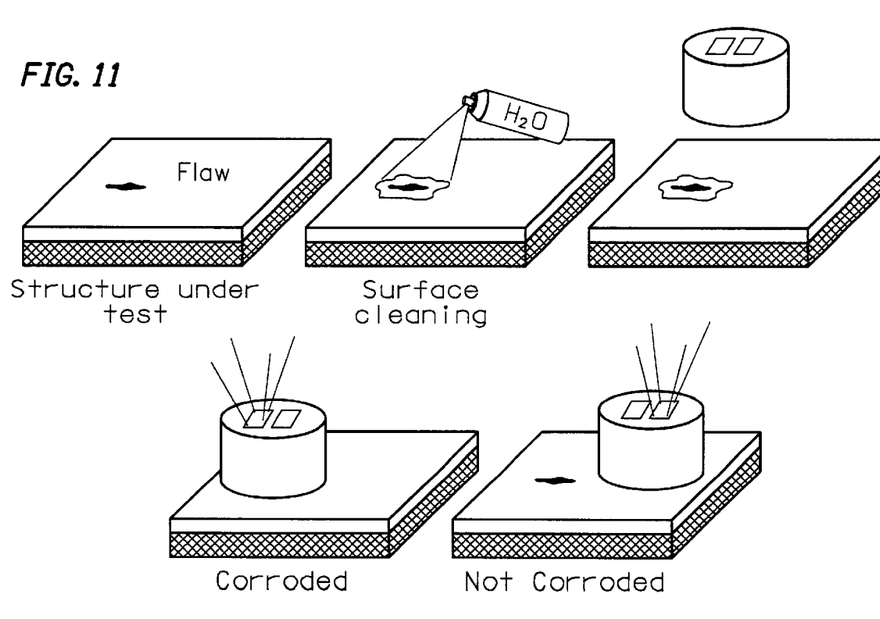
FIG. 11 is a process flow diagram illustrating the operational principle of the present invention.

FIG. 11 shows a summary of the operational principle of the sensor of the present invention. After a simple surface cleaning treatment which includes removing any dust and/or grease that may be on the surface of the substrate by washing with a surfactant or degreasing solution such as soap and water, (with a last step of humidifying the surface), the sensor will be placed on the surface to be inspected. Here, the impedance of the surface being tested is determined by applying a small sinusoidal voltage (e.g., 50 mV) and measuring the AC current response using a Solartron 1260 Impedance/Gain Phase analyzer interfaced with an EG&G PAR Potentiostat/Galvanostat Model 1273. The signal is applied at one frequency (e.g., 10 Hz) and the impedance value will be measured several times (e.g., 10 times), and an average impedance value will be obtained. It is possible to do this with a simple impedance analyzer unit controlled by a microprocessor either commercially available or custom designed. It is expected that the inspection of the area being tested will not take more than a few seconds (ca. less than 5 s). Comparison of the impedance value with a reference value contained in the memory of the sensor will indicate whether the area being tested is corroded or not. The sensor can be scanned over an entire surface manually or using a robotized arm. If a large sensor is used, once a problematic area is found, it is preferred that a smaller sensor be used to further localize the corroded site.

EXAMPLE 6

Figure 12:
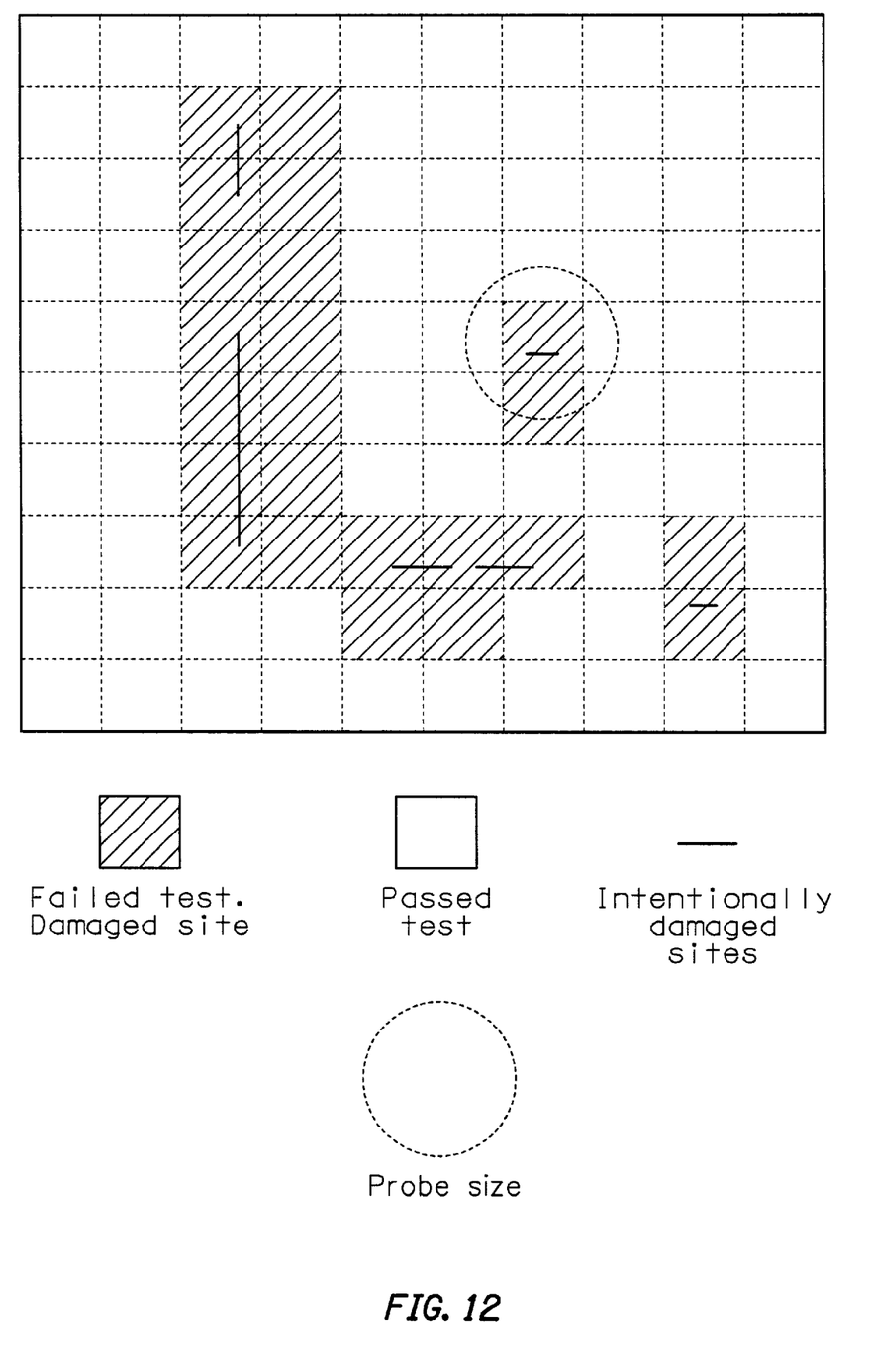
FIG. 12 is a schematic diagram for a scanning test of a 900 cm$^2$ painted Al7075-T6 coupon with a 20 cm$^2$ sensor of the present invention.

The sensor of this invention was tested on a 900 cm$^2$ painted Alclad 7075-T6 coupon. The coupon contained six intentionally damaged sites (flaws) of different sizes, and was inspected with a sensor having a contact area of 20 cm$^2$. The impedance magnitude was obtained at 10 Hz when a 50 mV voltage was applied. The sensor was placed on the surface of the coupon every 2.5 cm, so that the whole area was inspected. The value of the impedance magnitude was recorded for each site. It was found that when the sensor was located on a site that contained a flaw or part of a flaw, the impedance magnitude was considerably lower than the reference value (i.e., the value of the impedance magnitude for a flaw-free surface). FIG. 12 shows a diagram of the coupon with the flaws. The shadowed areas correspond to sites that "failed" the inspection (i.e., areas with damaged sites). In these shadowed areas, the value of the impedance magnitude was considerably lower than the reference value.

Figure 13:
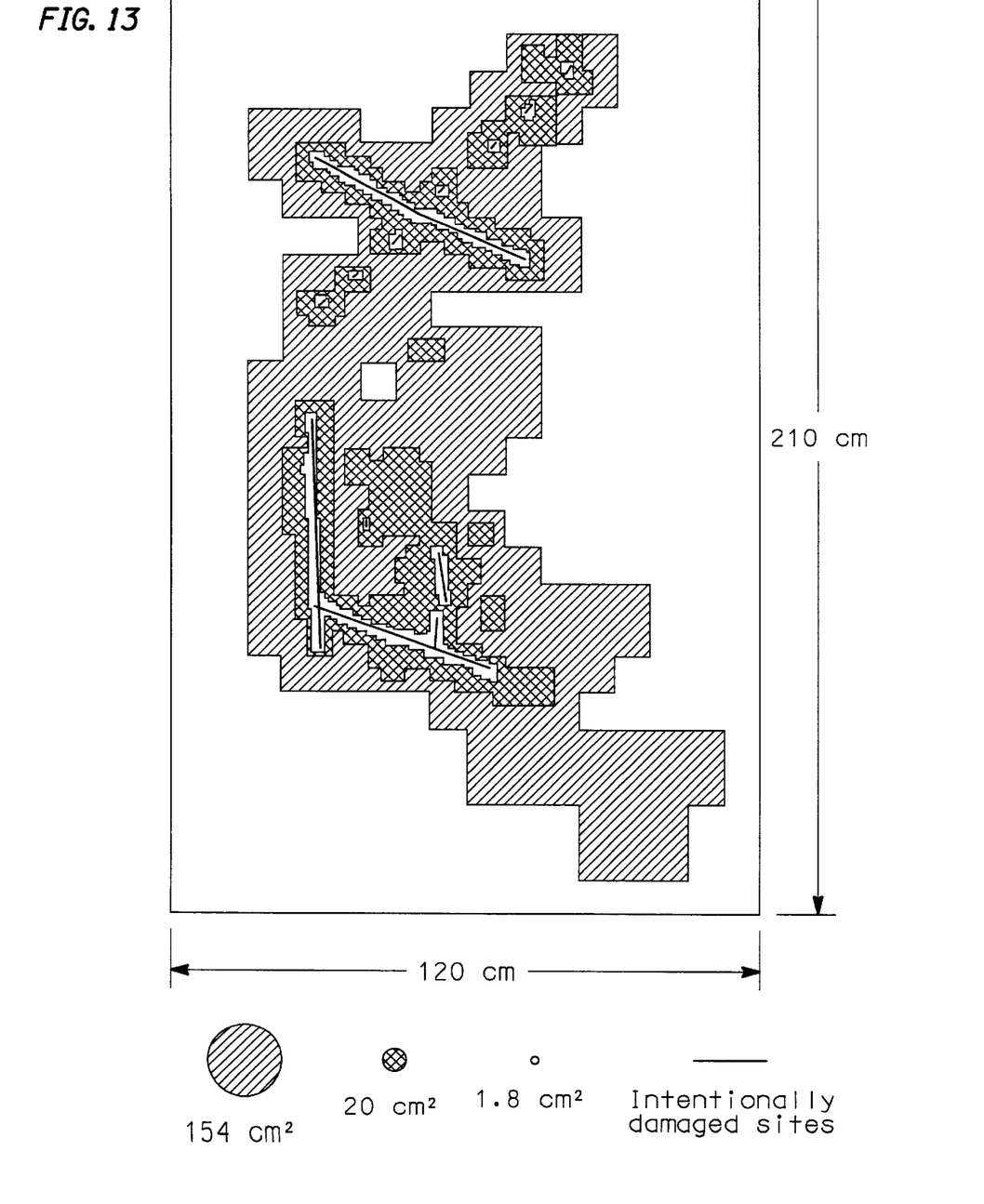
FIG. 13 is a schematic diagram for a scanning test of a 25,200 cm² painted A17075-T6 coupon with three different sensor sizes (154, 20, and 1.8 cm²) in accordance with the present invention.

FIG. 13 shows the performance of three sensors (154, 20, and 1.8 cm$^2$) on a 25,200 cm$^2$ painted Alclad 7075-T6 coupon. The coupon had intentionally damaged sites. The first step was to inspect the entire surface with the largest sensor. When the impedance value at 10 Hz was less than the reference value (i.e., the value of the impedance magnitude corresponding to a damaged-free surface), the areas were identified as "failed" (i.e., shadowed areas in FIG. 13). Next, the "failed" areas were inspected with the 20 cm$^2$ sensor to localize the flaw position, showing also some damage-free sections. Further localization of the flaws on the substrate was carried out by using the 1.8 cm$^2$ sensor. In addition to the intentionally damaged sites, a few other damaged sites were also localized. This successive inspection with sensors of different sizes reduces the time and labor required to inspect a wide area of a substrate in comparison to other procedures that are limited to a smaller probe size.

Figure 14:
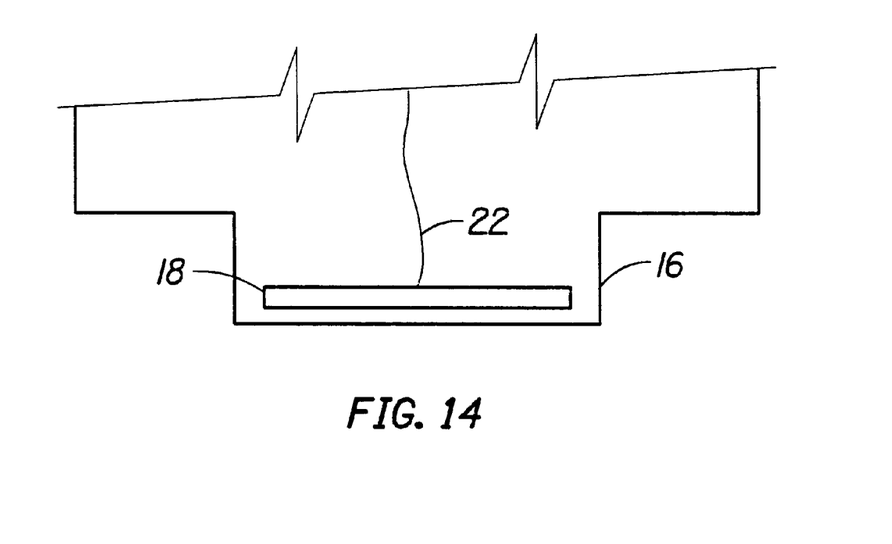
FIG. 14 is a schematic diagram of a sensor in accordance with the present invention.

FIG. 14 is a schematic diagram of a sensor of the present invention, where the bottom of the sensor has a stepped configuration. The solid electrolyte 16 is shown in a spaced relationship from the counter electrode 18. The solid electrolyte 16 is made of a flexible material, such as NAFION, that can be easily shaped in any number of ways, including concave, convex angular, stepped or flat, to suit the particular substrate being inspected. This is particularly useful for efficiently inspecting surfaces that have different angles.

Figure 15:
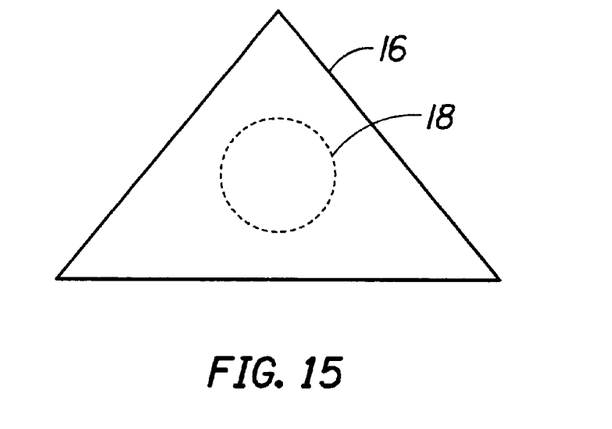
FIG. 15 is a bottom view of a sensor in accordance with the present invention.

FIG. 15 is a bottom view of a sensor of the present invention. The solid electrolyte 16 is in the shape of a triangle and the counter electrode 18 is shown in dotted lines. The sensor may be made in different shapes to suit a particular substrate, for instance the triangular shape may be useful for inspecting a substrate that has corner areas.

The sensor and the method for diagnosing the presence of damaged sites and corroded areas in painted metallic substrates have been described as being applied to aircraft structural metal alloys, but the sensor and method can also be applied to other objects including bare and painted metallic structures.

While the foregoing is directed to the preferred embodiment of the present invention, other and further embodiments of the invention may be devised without departing from the basic scope thereof, and the scope thereof is determined by the claims which follow.

What is claimed is:

1. An apparatus for detecting corrosion in an electronically conducting metal substrate comprising:
   (a) a housing having an open end portion;
   (b) a solid polymer electrolyte membrane coupled over the open end portion of the housing and having a first exposed surface adapted to be positionable in contact with a surface of the substrate; and
   (c) an electrode disposed in the housing and in electrochemical communication with a second surface of the solid polymer electrolyte membrane, wherein the first exposed surface of the membrane directly opposes the electrode.

2. The apparatus of claim 1, further comprising a biasing member disposed in the housing.

3. The apparatus of claim 1, wherein at least a portion of the housing is made of an electronically and ionically insulating material.

4. The apparatus of claim 1, wherein the solid polymer electrolyte membrane is an ion exchange membrane.

5. The apparatus of claim 1, wherein the solid polymer electrolyte membrane is electronically insulating.

6. The apparatus of claim 4, wherein the ion exchange membrane comprises an ion exchange material selected from perfluorinated sulfonic acid polymers, perfluorinated carboxylic acid polymers, perfluoro bisulfonimide polymers, perfluoro phosphonic acid polymers, perfluorinated tetraalkylammonium salt polymers, carbanion acids, and mixtures thereof.

7. The apparatus of claim 1, wherein the solid polymer electrolyte membrane has a charge carrier comprising a non-corrosive ion.

8. The apparatus of claim 7, wherein the charge carrier is a cation.

9. The apparatus of claim 7, wherein the charge carrier is an anion.

10. The apparatus of claim 1, wherein the apparatus is a self-contained leak-proof unit.

11. The apparatus of claim 1, further comprising a current conductor attached to the electrode.

12. The apparatus of claim 2, wherein the housing has an inside surface defining a cavity and a support means positioned within the cavity, wherein the support means defines a bore extending therethrough that is in flow communication with the solid polymer electrolyte membrane, wherein the bore through the support means is at least partially filled with fluid.

13. The apparatus of claim 12, wherein the biasing member is positioned between a support means and the electrode, wherein the biasing member defines a bore therethrough that is in axial alignment with the bore defined by the support means.

14. The apparatus of claim 13, wherein the bore through the support means contains water.

15. The apparatus of claim 13, wherein the bore through the support means contains a liquid electrolyte.

16. The apparatus of claim 1, wherein the electrode comprises a material, wherein the material is a platinum group metal, a gold group metal, tungsten, titanium, zirconium, stainless steel, carbon, conductive oxides, platinum group metal oxides, gold group metal oxides, tungsten oxide, tin oxide, or mixtures thereof.

17. The apparatus of claim 1, wherein the electrode comprises a coated material, wherein the coating is a platinum group metal, a gold group metal, tungsten, titanium, zirconium, stainless steel, carbon, conductive oxides, platinum group metal oxides, gold group metal oxides, tungsten oxide, tin oxide, or mixtures thereof.

18. The apparatus of claim 16, wherein the material is metal sheet, metal gauze, or thin film.

19. The apparatus of claim 1, further comprising a sealing member for sealing the solid electrolyte to the housing.

20. The apparatus of claim 19, wherein the sealing member comprises a first o-ring positioned between the housing and the solid polymer electrolyte membrane, a worm gear positioned around the solid electrolyte and a second o-ring positioned between the worm gear and the solid polymer electrolyte membrane.

21. The apparatus of claim 2, further comprising an inert insulating member positioned between the biasing member and the electrode.

22. The apparatus of claim 21, wherein the inert insulating member is a polytetrafluoroethylene tape.

23. The apparatus of claim 1, wherein the electrode is in physical contact with the solid polymer electrolyte membrane.

24. The apparatus of claim 1, wherein the open end portion of the housing has a shape selected from generally angular, stepped, concave, convex, and flat.

25. The apparatus of claim 1, wherein the solid polymer electrolyte membrane has an area of from about $0.1$ $cm^2$ to about $10,000$ $cm^2$.

26. The apparatus of claim 24, wherein the solid polymer electrolyte membrane has an area of from about $1.8$ $cm^2$ to about $154$ $cm^2$.

27. An apparatus for analyzing corrosion comprising:
   (a) a solid polymer electrolyte membrane having a first exposed surface adapted to be positionable in contact with a surface of a substrate;
   (b) an electrode in electrochemical communication with a second surface of the solid polymer electrolyte membrane; and
   (c) a source of a fluid for hydrating the solid polymer electrolyte membrane.

28. The apparatus of claim 27, wherein the solid polymer electrolyte membrane is made of an electronically insulating, ionically conducting material.

29. The apparatus of claim 27, wherein the solid polymer electrolyte membrane contains a non-corrosive ion.

30. The apparatus of claim 27, wherein the solid polymer electrolyte membrane is saturated with water.

31. The apparatus of claim 27, wherein the source of fluid comprises a housing in fluid communication with the solid polymer electrolyte membrane.

32. An apparatus for analyzing corrosion comprising:
   (a) a sensor having a solid polymer electrolyte membrane, an electrode in electrochemical communication with the solid polymer electrolyte membrane, and a source of a fluid for hydrating the solid polymer electrolyte membrane; and
   (b) an impedance measuring instrument in electrical contact with the electrode.

33. The apparatus of claim 32, wherein the solid polymer electrolyte membrane is made of an electronically insulating, ionically conducting material.

34. The apparatus of claim 32, wherein the solid polymer electrolyte membrane contains a non-corrosive ion.

35. The apparatus of claim 32, wherein the solid polymer electrolyte membrane is saturated with water.

36. The apparatus of claim 32, wherein the impedance measuring element is adapted to generate an AC signal at a selected frequency, measure the perturbed signal, and calculate the corresponding impedance of a substrate being tested.

37. The apparatus of claim 32, wherein the source of fluid comprises a housing in fluid communication with the solid polymer electrolyte.

38. The apparatus of claim 32, wherein at least a portion of the housing is made of an electronically and ionically insulating material.

39. The apparatus of claim 1, wherein the electrode comprises a platinum group metal selected from platinum, iridium, rhodium and ruthenium.

40. An apparatus for detecting corrosion in an electronically conducting metal substrate comprising:
   (a) a housing having an open end portion;
   (b) a solid polymer electrolyte membrane coupled over the open end portion of the housing and having a first exposed surface adapted to be positionable in contact with a surface of the substrate;
   (c) an electrode disposed in the housing and in electrochemical communication with a second surface of the solid polymer electrolyte membrane; and
   (d) a voltage source having a first terminal in electronic communication with the electrode and a second terminal in electronic communication with the substrate for providing an AC source voltage at a selected frequency.

41. The apparatus of claim 40, wherein the voltage source applies voltage at a single frequency.

42. The apparatus of claim 40, further comprising an impedance measuring instrument in electronic communication between the electrode and the substrate for measuring impedance indicative of resistance of the substrate.

43. An apparatus for detecting corrosion in an electronically conducting metal substrate comprising:
   (a) a housing having an open end portion;
   (b) a solid polymer electrolyte membrane coupled over the open end portion of the housing and having a first exposed surface adapted to be positionable in contact with a surface of the substrate; and
   (c) an electrode disposed in the housing and in electrochemical communication with a second surface of the solid polymer electrolyte membrane, wherein the first surface of the membrane is free from electrodes.

44. An apparatus for detecting corrosion in an electronically conducting metal substrate comprising:
   (a) a housing having an open end portion;
   (b) a solid polymer electrolyte membrane coupled over the open end portion of the housing and having a first exposed surface adapted to be positionable in contact with a surface of the substrate; and
   (c) a thin film electrode fixed to a second surface of the solid polymer electrolyte membrane.

45. An apparatus for detecting corrosion in an electronically conducting metal substrate comprising:
   (a) a housing having an open end portion;
   (b) a solid polymer electrolyte membrane coupled over the open end portion of the housing and having a first exposed surface adapted to be positionable in contact with a surface of the substrate; and
   (c) an electrode disposed in the housing; and
   (d) a biasing member disposed in the housing to urge the electrode into contact with a second surface of the solid polymer electrolyte membrane and urge the solid electrolyte into contact with the substrate.

46. The apparatus of claim 17, wherein the platinum group metal oxides are selected from iridium oxide, rhodium oxide and ruthenium oxide.

47. The apparatus of claim 40, wherein the voltage source applies voltage at multiple frequencies.

* * * * *